United States Patent [19]

Diekmann

[11] Patent Number: 4,725,348
[45] Date of Patent: Feb. 16, 1988

[54] DEVICE FOR THE ELUTION OF ELECTRICALLY-CHARGED MACROMOLECULES

[75] Inventor: Stephan Diekmann, Bovenden, Fed. Rep. of Germany

[73] Assignee: Max-Planck-Gesellschaft Zur Foerderung der Wissenschaften e.V., Goettingen, Fed. Rep. of Germany

[21] Appl. No.: 730,376

[22] Filed: May 3, 1985

[30] Foreign Application Priority Data

May 9, 1984 [DE] Fed. Rep. of Germany ....... 3417180

[51] Int. Cl.⁴ .................... G01N 27/28; G01N 33/68
[52] U.S. Cl. ............................. 204/299 R; 204/182.8
[58] Field of Search ..................... 204/182.8, 299 R

[56] References Cited

U.S. PATENT DOCUMENTS 3,989,612 11/1976 Kragt et al. .................. 204/182.1
4,049,534 9/1977 Posner ......................... 204/299 R
4,576,702 3/1986 Peck et al. ................... 204/299 R

FOREIGN PATENT DOCUMENTS 552373 4/1977 U.S.S.R. .

OTHER PUBLICATIONS

Diekmann, S., "A Device to Elute Biomolecules Out of Gels", *Electrophoresis* '84, Editor: Volker Neuhoff, pp. 154–155, Jul. 1984.

*Primary Examiner*—T. Tung
*Assistant Examiner*—William T. Leader
*Attorney, Agent, or Firm*—Felfe & Lynch

[57] ABSTRACT

The present invention provides a device for the elution of electrically-charged macromolecules, especially biopolymers, from a gel by electrophoretic transfer of the macromolecules from a gel placed under a buffer into a salt solution, said device having a container (2) for the reception of an electrolyte, which chamber is divided up by at least one reception chamber for a piece of gel, which reception chamber is permeable to the electrolyte, into two electrode chambers (12, 14), each of which contains at least one electrode (8, 10), wherein the electrode chambers (12, 14) are separated from one another by a block (4) provided with a closable electrolyte passage (6) and the at least one reception chamber for a piece of gel is formed by a trough (16) let into the surface of the block (4), which trough is connected via at least one first opening (20), present in or next to the bottom (18) thereof, with one electrode chamber (14) and via a second opening (22), present in or next to the bottom thereof with a canal (24), which first descends and then rises, opening into the other electrode chamber (12) for the reception of the salt solution.

5 Claims, 3 Drawing Figures

U.S. Patent  Feb. 16, 1988  4,725,348
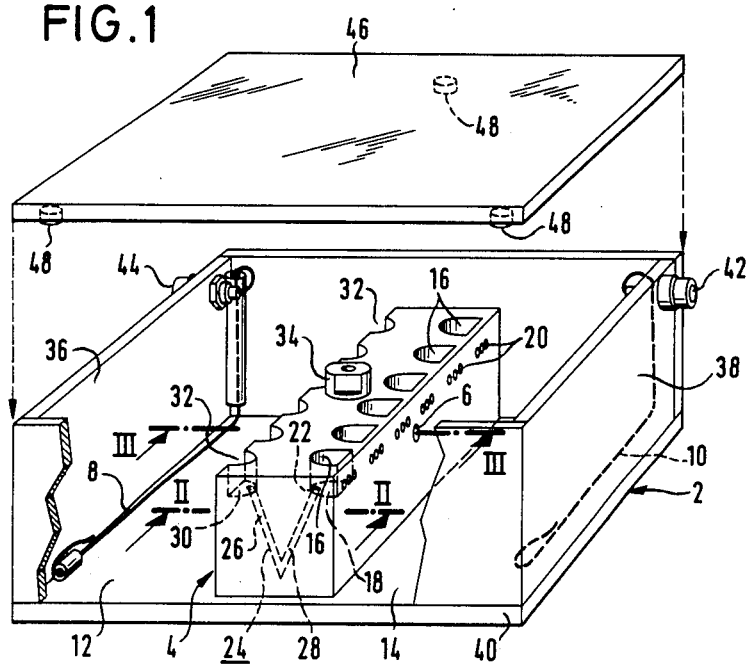
FIG.1
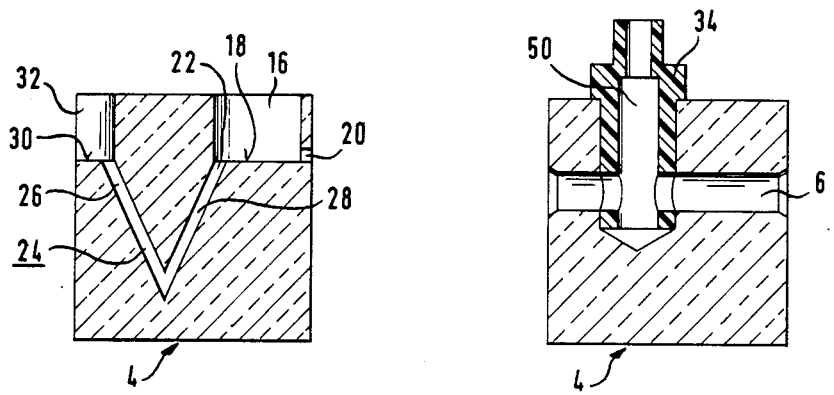
FIG.2
FIG.3

DEVICE FOR THE ELUTION OF ELECTRICALLY-CHARGED MACROMOLECULES

The present is concerned with a device for the elution of electrically-charged macromolecules, especially biopolymers, from a gel by electrophoretic transfer of the macromolecules from the gel placed under a buffer into a salt solution.

In the case of a device of this kind known from U.S. Pat. No. 3,989,612, between the electrode chambers there lies a gel reception chamber which is accessible from the electrode chambers through windows. The gel reception chamber can only accommodate one piece of gel. The eluted, electrically-charged macromolecules pass into one of the electrode chambers and have only a comparatively low concentration in the electrolytes present therein. In order to replace a piece of gel, the device must be dismantled into a number of parts. Corresponding features are also displayed by a device known from U.S. Pat. No. 4,049,534.

It is an object of the present invention to provide a simply constructed device of the kind mentioned initially which is simple to handle, gives a high yield of macromolecules, especially of biopolymers, in a comparatively short time and requires practically no servicing.

Thus, according to the present invention, there is provided a device for the elution of electrically-charged macromolecules, especially biopolymers, from a gel by electrophoretic transfer of the macromolecules from a gel placed under a buffer into a salt solution, said device having a container for the reception of an electrolyte, which chamber is divided up by at least one reception chamber for a piece of gel, which reception chamber is permeable to the electrolyte, into two electrode chambers, each of which contains at least one electrode, wherein the electrode chambers are separated from one another by a block provided with a closable electrolyte passage and at least one reception chamber for a piece of gel is formed by a trough let into the surface of the block, which trough is connected via at least one first opening, present in or next to the bottom thereof, with one electrode chamber and via a second opening, present in or next to the bottom thereof, with a canal, which first descends and then rises, opening into the other electrode chamber for the reception of the salt solution.

For using the device, the electrolyte passage is first opened and the container is then filled with the electrolyte of low concentration, which also serves as buffer, taking care that the electrolyte moistens all surfaces with which it comes into contact, and the electrodes are connected, possibly for control reasons, to a test voltage in order to ascertain the electric current through the electrolyte. The electrolyte level is then decreased to below the bottom of the trough present in the block and possibly also to below a seat-shaped recess described hereinafter. The canal which first descends and then rises can be incorporated into the block and opens into or next to the bottom of the above-mentioned seat-shaped recess which is on the side of the block facing the other electrode chamber. Subsequently, pieces of gel are placed into the troughs, for example one piece of gel per trough, and the electrolyte level is raised until each piece of gel is covered by the electrolyte. Thereafter, a salt solution of high concentration, which is possibly coloured, is introduced into each of the canals used for the elution and finally the electrolyte passage in the block is closed.

The electrolysis is now carried out by application of a voltage. The macromolecules migrate in the electric field out of the piece of gel into the electrolyte in the corresponding canal and there into the salt solution of high concentration. The migration can possibly be monitored with parallel migrating coloured materials. The macromolecules, especially biopolymers, become concentrated upon entry into the salt solution of high concentration. When the pieces of gel have been eluted, the voltage is switched off and the electrolyte passage is opened. By electrolyte removal from the electrolyte passage, the electrolyte level is then again lowered to below the bottom of the trough and possibly the seat-shaped recesses and the salt solution with the macromolecules present therein, especially biopolymers, is pipetted out of the canals. By introducing the salt solution which has been pipetted out into ethanol, the biopolymers and especially nucleic acids, can be precipitated in known manner.

It is especially noteworthy that, when using the device according to the present invention, the biopolymers and especially nucleic acids only come into contact with materials and chemicals with which they come into contact in any case during conventional working steps.

According to a preferred embodiment of the present invention, the canal which first descends and then rises is V-shaped. Furthermore, the electrolyte passage can run under the bottoms of the trough and the seat-shaped recess. In addition, a plug of a cock with an axial connection bore, which is accessible from its upper side, can be let into the block.

One embodiment of the present invention will now be described in more detail with reference to the accompanying drawings, in which:

FIG. 1 is a perspective view of one embodiment of the device;

FIG. 2 is a section along the line II—II in FIG. 1; and

FIG. 3 is a section along the line III—III in FIG. 1.

The device comprises a container 2 for the reception of an electrolyte, which container 2 is divided by a block 4 having a closable electrolyte passage 6 into two electrode chambers 12, 14, each containing an electrode 8, 10. In the surface of the block 4 are let in a series of six adjacent troughs 16, each serving for the reception of a piece of gel. Each trough 16 is connected with the electrode chamber 14 via three first openings 20 present in the side wall thereof next to the bottom 18 thereof and via an opening 22 present in the bottom 18 thereof with a canal 24, which first descends and then rises, opening into the electrode chamber 12, this canal 24 serving for the reception of the salt solution. Each canal 24 consists of two straight sections 26, 28, which together form a V, these sections 26, 28 being bored into the block 4. In the case of the present example, the canal 24 opens on the side of the electrode chamber 12 into the bottom 30 of a seat-shaped recess 32 in the block.

The passage 6 runs under the bottom 18 of the troughs 16 and the bottom 30 of the seat-shaped recesses 32.

Into the block 4, there is let in from above a rotatable plug of a cock 34 with an axial connection bore 50, which plug passes through the passage 6.

The container 2 consists of a transparent synthetic resin. The electrodes 8, 10 are wires which are placed along opposite-lying walls 36, 38 of the container 2 on the bottom 40 thereof and run upwardly to external connections 42, 44 next to opposite-lying points of the upper edge of the container 2.

The container is closed with a removable lid 46 which is provided on its lower side with projections 48 which prevent it sliding with regard to the container 2.

I claim:

1. A device for the elution of electrically-charged macromolecules, especially biopolymers, from a gel by electrophoretic transfer of the macromolecules from a gel placed under a buffer into a salt solution, said device comprising a container (2) for the reception of an electrolyte, which container is divided into two electrode chambers (12, 14) by a block (4) the surface of which contains at least one trough (16) adapted to receive a piece of gel, each electrode chamber containing at least one electrode (8, 10), wherein the electrode chambers (12, 14) are separated from one another by block (4) which is provided with a closable electrolyte passage (6) connecting the electrode chambers, each trough being connected via at least one first opening (20), present in or next to the bottom (18) of said trough with one electrode chamber (14) and via a second opening (22), present in or next to the bottom of said trough with a canal (24), which first descends and then rises, opening into the other electrode chamber (12) for the reception of the salt solution.

2. Device according to claim 1, characterised in that the canal (24) is incorporated into the block (4) and opens into or next to the bottom (30) of a seat-shaped recess (32) in the side of the block facing the other electrode chamber (12).

3. Device according to claim 2, characterised in that the passage (6) runs under the bottoms (18, 30) of the trough (16) and of the seat-shaped recess (32).

4. Device according to claim 1, characterised in that the canal (24) is V-shaped.

5. Device according to claim 1, characterised in that into the block (4) there is placed a plug of a cock (34), accessible from its upper side, with an axial connection bore (50).

* * * * *